(12) United States Patent
Nakatogawa

(10) Patent No.: US 11,988,932 B2
(45) Date of Patent: May 21, 2024

(54) IMAGING DEVICE WITH A LIQUID CRYSTAL PANEL IN FRONT OF AN IMAGE ELEMENT

(71) Applicant: Japan Display Inc., Tokyo (JP)

(72) Inventor: Hirondo Nakatogawa, Tokyo (JP)

(73) Assignee: Japan Display Inc., Tokyo (JP)

( * ) Notice: Subject to any disclaimer, the term of this patent is extended or adjusted under 35 U.S.C. 154(b) by 0 days.

(21) Appl. No.: 17/889,446

(22) Filed: Aug. 17, 2022

(65) Prior Publication Data
US 2023/0058518 A1    Feb. 23, 2023

(30) Foreign Application Priority Data
Aug. 19, 2021 (JP) ................. 2021-134015

(51) Int. Cl.
| | | |
|---|---|---|
| G02F 1/137 | (2006.01) | |
| A61B 1/045 | (2006.01) | |
| A61B 1/06 | (2006.01) | |
| G02F 1/133 | (2006.01) | |
| G02F 1/1333 | (2006.01) | |
| G02F 1/1343 | (2006.01) | |
| H04N 13/254 | (2018.01) | |
| H04N 13/296 | (2018.01) | |

(52) U.S. Cl.
CPC ............. *G02F 1/137* (2013.01); *A61B 1/045* (2013.01); *A61B 1/0655* (2022.02); *G02F 1/13306* (2013.01); *G02F 1/133308* (2013.01); *G02F 1/134309* (2013.01); *H04N 13/254* (2018.05); *H04N 13/296* (2018.05)

(58) Field of Classification Search
None
See application file for complete search history.

(56) References Cited

U.S. PATENT DOCUMENTS

| | | | | |
|---|---|---|---|---|
| 5,047,847 A | * | 9/1991 | Toda | H04N 23/75 349/1 |
| 5,097,352 A | * | 3/1992 | Takahashi | G02B 27/28 349/200 |
| 5,150,234 A | * | 9/1992 | Takahashi | G02F 1/29 349/1 |
| 5,222,477 A | * | 6/1993 | Lia | A61B 1/05 348/45 |
| 5,976,071 A | * | 11/1999 | Sekiya | H04N 13/243 348/45 |
| 2011/0115882 A1 | * | 5/2011 | Shahinian | A61B 1/00193 348/E13.001 |
| 2013/0321602 A1 | * | 12/2013 | Hayama | A61B 1/0655 348/68 |

(Continued)

FOREIGN PATENT DOCUMENTS

JP    2005-34654 A    2/2005

*Primary Examiner* — Ryan Crockett
(74) *Attorney, Agent, or Firm* — Michael Best & Friedrich LLP

(57) ABSTRACT

According to one embodiment, an imaging device includes a housing, an illumination device, an optical system that has at least one lens, a liquid crystal panel, and an imaging element that constitutes a camera together with the optical system. The incident light control area of the liquid crystal panel has a first region, a second region located so as to be shifted from the first region, and a third region other than the first region and the second region.

9 Claims, 12 Drawing Sheets

(56) References Cited

U.S. PATENT DOCUMENTS

| | | | |
|---|---|---|---|
| 2014/0085421 A1* | 3/2014 | Kuth | G02B 23/2484 348/45 |
| 2019/0058819 A1* | 2/2019 | Kobayashi | G02B 23/2446 |
| 2021/0106207 A1* | 4/2021 | Matsumoto | A61B 1/000094 |

* cited by examiner

IMAGING DEVICE WITH A LIQUID CRYSTAL PANEL IN FRONT OF AN IMAGE ELEMENT

CROSS-REFERENCE TO RELATED APPLICATIONS

This application is based upon and claims the benefit of priority from Japanese Patent Application No. 2021-134015, filed Aug. 19, 2021, the entire contents of which are incorporated herein by reference.

FIELD

Embodiments described herein relate generally to an imaging device.

BACKGROUND

As a device used by being inserted into a narrow space such as an inside of a body or an inside of a tube, an imaging device is known. For example, an endoscope is known as an imaging device for capturing images of the inside of the body. The endoscope includes a main body and a connection cable connected to the main body. When an endoscope is used, after the main body of the endoscope is inserted into the body, a forward action to insert the connection cable further into the body and a backward action to draw the connection cable from inside the body are performed.

The main body includes a cylindrical housing and two cameras accommodated in the housing. The housing has one end surface and another end surface on the opposite side to the one end surface. Two incident ports for exposing two camera lenses are formed in one end surface of the housing. An insertion port through which the connection cable passes is formed in the other end surface of the housing, and the connection cable is connected to each of the two cameras inside the housing. The foregoing endoscope is capable of imaging the inside of the body using a twin-lens camera, and of capturing a stereoscopic image and a stereoscopic video.

DETAILED DESCRIPTION

Figure 1:
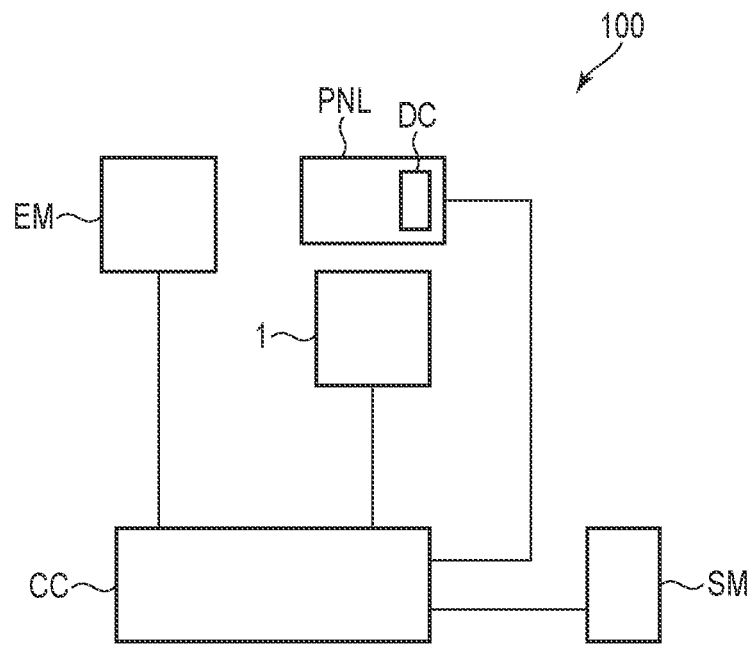
FIG. 1 is a block diagram illustrating an imaging device according to a first embodiment.

In general, according to one embodiment, there is provided an imaging device comprising: a housing having a cylindrical shape that includes a central axis, and an emission port and an incident port that are opened in one end surface in a direction along the central axis; an illumination device that is accommodated in the housing, and that faces the emission port and illuminates a front side of the one end surface through the emission port; an optical system that is accommodated in the housing, and that faces the incident port and has at least one lens; a liquid crystal panel that is located closer to the outside of the housing than the optical system, and that has an incident light control area and covers each of the entire incident port and the entire optical system when viewed from a direction perpendicular to the one end surface; and an imaging element that is accommodated in the housing, that constitutes a camera together with the optical system, and that acquires information about light falling incident from outside the housing through the incident port, the incident light control area of the liquid crystal panel, and the optical system. The incident light control area has a first region, a second region located so as to be shifted from the first region, and a third region other than the first region and the second region.

According to another embodiment, there is provided an imaging device comprising a housing having a cylindrical shape that includes a central axis, and an emission port and an incident port that are opened in one end surface in a direction along the central axis;

an illumination device that is accommodated in the housing, and that faces the emission port and illuminates a front side of the one end surface through the emission port; an optical system that is accommodated in the housing, and that faces the incident port and has at least one lens; a liquid crystal panel that is located closer to the outside of the housing than the optical system, and that has an incident light control area and covers each of the entire incident port and the entire optical system when viewed from a direction perpendicular to the one end surface; and an imaging element that is accommodated in the housing, that constitutes a camera together with the optical system, and that acquires information about light falling incident from outside the housing through the incident port, the incident light control area of the liquid crystal panel, and the optical system. The liquid crystal panel switches the incident light control area to a light control pattern. When switching to the light control pattern, the liquid crystal panel sets a plurality of first regions that are located in a dispersed manner in the incident light control area to a non-transmissive state, and sets a plurality of second regions other than the plurality of first regions in the incident light control area to a transmissive state.

Embodiments will be described hereinafter with reference to the accompanying drawings. The disclosure is merely an example, and proper changes within the spirit of the invention, which are easily conceivable by a skilled person, are included in the scope of the invention as a matter of course. In addition, in some cases, in order to make the description clearer, the widths, thicknesses, shapes, etc., of the respective parts are schematically illustrated in the drawings, compared to the actual modes. However, the schematic illustration is merely an example, and adds no restrictions to the interpretation of the invention. Besides, in the specification and drawings, the same or similar elements as or to those described in connection with preceding drawings or those exhibiting similar functions are denoted by like reference numerals, and a detailed description thereof is omitted unless otherwise necessary.

First Embodiment

First, a first embodiment will be described.

FIG. 1 is a block diagram illustrating an imaging device 100 according to the first embodiment. The imaging device 100 is used by being inserted into a narrow space such as an inside of a body or an inside of a tube. The imaging device 100 of the first embodiment is an endoscope for capturing images inside the body.

As illustrated in FIG. 1, the imaging device 100 includes an illumination device EM, a camera 1, a liquid crystal panel PNL, a driving circuit DC, a controlling circuit CC, and a storage medium SM. The controlling circuit CC is connected to the illumination device EM, the liquid crystal panel PNL, the camera 1, and the storage medium SM.

The driving circuit DC is mounted on the liquid crystal panel PNL and is connected to the controlling circuit CC via the liquid crystal panel PNL. Note that the imaging device 100 may have an electrical system in which the controlling circuit CC and the liquid crystal panel PNL are connected via the driving circuit DC.

The controlling circuit CC controls driving of the driving circuit DC, the liquid crystal panel PNL, the illumination device EM, and the camera 1. The controlling circuit CC is capable of storing, on the storage medium SM, data (for example, image data) that is detected by the camera 1.

Figure 2:
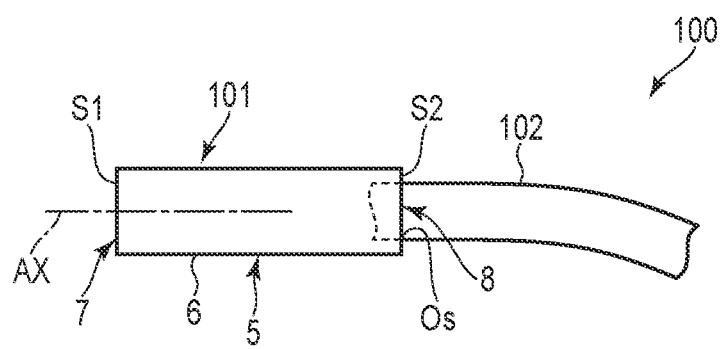
FIG. 2 is a side elevational view illustrating the imaging device.

FIG. 2 is a side elevational view illustrating the imaging device 100. As illustrated in FIG. 2, the imaging device 100 includes a main body 101, and a connection cable 102 connected to the main body 101. The main body 101 has a housing 5. The housing 5 has a cylindrical shape that includes a central axis AX. The housing 5 has a cylindrical portion 6, an end plate 7 that closes one end of the cylindrical portion 6, and an end plate 8 that closes the other end of the cylindrical portion 6. The cylindrical portion 6, the end plate 7, and the end plate 8 are integrally formed. Each of the end plates 7 and 8 is a circular plate.

The housing 5 has one end surface S1 located at one end in the direction along the central axis AX and another end surface S2 on the opposite side to the one end surface S1. The end plate 7 has one end surface S1, and the end plate 8 has the other end surface S2. A through-hole is formed in the end plate 8, and an insertion port Os, which is connected to the through-hole, is opened in the other end surface S2. The connection cable 102 passes through the insertion port Os of the housing 5 and is fixed to the housing 5.

In the present embodiment, the controlling circuit CC is located inside the housing 5, and the connection cable 102 is connected to the controlling circuit CC. Note that the controlling circuit CC may be located outside the housing 5. In this case, the connection cable 102 connects the controlling circuit CC and electronic components such as the illumination device EM, the liquid crystal panel PNL, and the camera 1.

When the imaging device 100 is used, after the main body 101 is inserted into the body, a forward action to insert the connection cable 102 further into the body and a backward action to draw the connection cable 102 from inside the body are performed.

Figure 3:
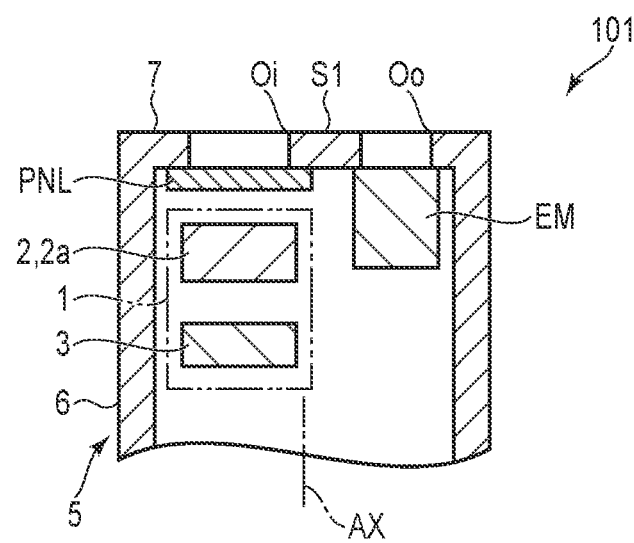
FIG. 3 is a cross-sectional view illustrating a portion of the main body illustrated in FIG. 2.

FIG. 3 is a cross-sectional view illustrating a portion of the main body 101 illustrated in FIG. 2. As illustrated in FIG. 3, the housing 5 has an emission port Oo and an incident port Oi that are open in the one end surface S1. The emission port Oo is connected to a through-hole formed in the end plate 7, and the incident port Oi is connected to another through-hole formed in the end plate 7. In the present embodiment, the one end surface S1 is a plane and is parallel to a plane perpendicular to the central axis AX. However, the one end surface S1 may be inclined with respect to the plane perpendicular to the central axis AX.

The illumination device EM is accommodated in the housing 5 and is fixed to the housing 5. The illumination device EM faces the emission port Oo. For example, the illumination device EM is fixed to the surface of the end plate 7 on the opposite side to the one end surface S1. The illumination device EM is, for example, a light-emitting diode (LED), and emits white illumination light (visible light). The illumination device EM is configured to illuminate a front side of the one end surface S1 through the emission port Oo. For this reason, the illumination device EM is capable of illuminating a subject to be imaged by the camera 1.

The camera 1 has an optical system 2 and an imaging element (image sensor) 3. The optical system 2 is accommodated in the housing 5 and fixed to the housing 5. The optical system 2 has at least one lens 2a. The optical system 2 faces the incident port Oi.

The imaging element 3 is accommodated in the housing 5 and is fixed to the housing 5. The driving of the imaging element 3 is controlled by the controlling circuit CC illustrated in FIG. 1. The optical system 2 is located between the incident port Oi and the imaging element 3. The imaging element 3 constitutes the camera 1 together with the optical system 2. Note that the imaging element 3 and the optical system 2 may be assembled into a module, and in this case, the module is accommodated in the housing 5 and is fixed to the housing 5.

The liquid crystal panel PNL is located closer to the outside of the housing 5 than the optical system 2, and is fixed to the housing 5. The liquid crystal panel PNL faces the incident port Oi. Note that the optical system 2 is located between the liquid crystal panel PNL and the imaging element 3. In the present embodiment, the liquid crystal panel PNL is accommodated in the housing 5 and is fixed to the surface of the end plate 7 on the opposite side to the one end surface S1.

The end plate 7, the liquid crystal panel PNL, the optical system 2, and the imaging element 3 are arranged side by side in that order in the direction along the central axis AX. The imaging element 3 is capable of acquiring information about light falling incident from outside the housing 5 through the incident port Oi, the incident light control area of the liquid crystal panel PNL, and the optical system 2. Note that details of the incident light control area will be described subsequently.

Figure 4:
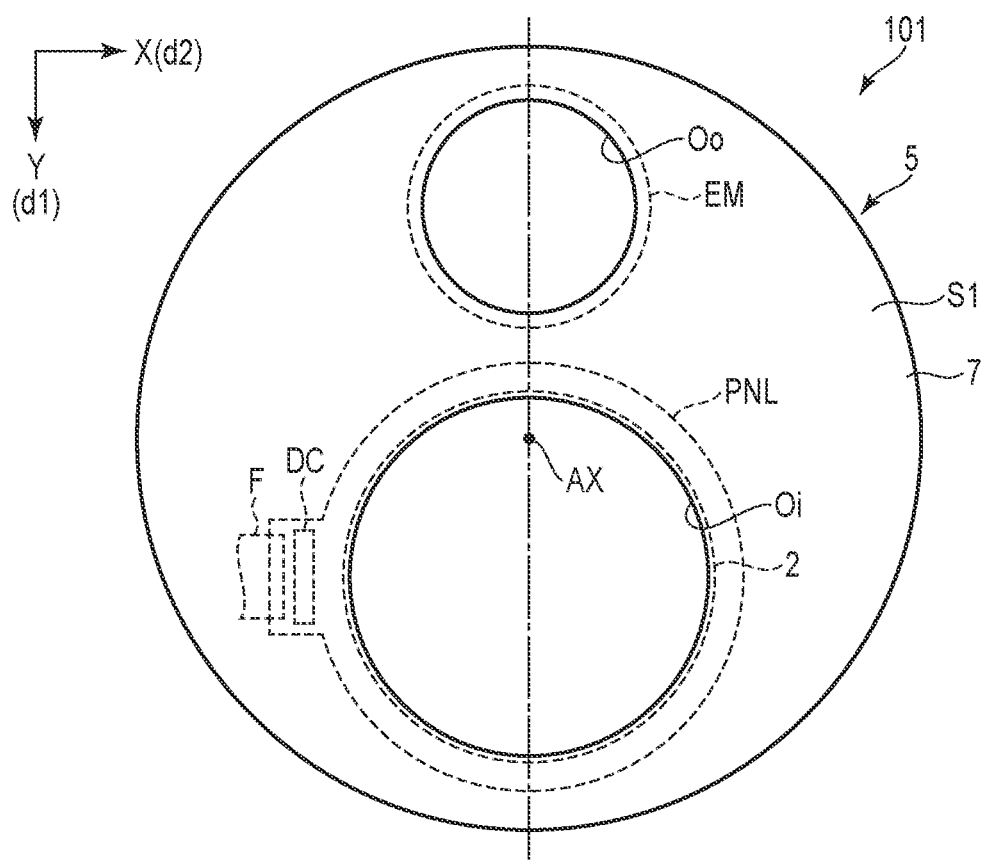
FIG. 4 is a front view of the main body illustrated in FIG. 3 as viewed from a direction perpendicular to one end surface.

FIG. 4 is a front view of the main body 101 illustrated in FIG. 3 as viewed from a direction perpendicular to the one end surface S1. In the drawing, a straight line passing through the central axis AX is denoted by one dot chain line.

As illustrated in FIG. 4, the emission port Oo and the incident port Oi each have a circular shape. In the present embodiment, the emission port Oo and the incident port Oi each have a perfect circle shape. When the emission port Oo and the incident port Oi are viewed from a direction parallel to the central axis AX, the size of the incident port Oi is larger than the size of the emission port Oo.

The emission port Oo and the incident port Oi are arranged side by side in a diametrical direction d1 of the one end surface S1. For this reason, in comparison with a case where the emission port Oo and the incident port Oi are not arranged side by side in the diametrical direction d1, the one end surface S1 can be reduced, and furthermore, the main body 101 can be downsized.

Furthermore, the imaging device 100 is configured to image a subject using a monocular camera. The incident port open in the one end surface S1 is an incident port Oi for the camera 1. In comparison with a case where a plurality of incident ports is opened in the one end surface S1, the one end surface S1 can be reduced, and furthermore, the main body 101 can be downsized.

The illumination device EM faces the whole of the emission port Oo. The liquid crystal panel PNL has a plane parallel to an X-Y plane defined by a direction X and a direction Y that are orthogonal to each other. In the present embodiment, the X-Y plane is parallel to the one end surface S1. The liquid crystal panel PNL covers the whole of the incident port Oi and the whole of the optical system 2 when viewed from a direction perpendicular to the one end surface S1.

Note that the optical system 2 has a circular shape, and the center of the optical system 2 (lens 2a) is eccentric from the central axis AX. The size of the liquid crystal panel PNL is larger than the size of the optical system 2.

The imaging device 100 further includes a wiring substrate F. The wiring substrate F is formed by a flexible printed circuit (FPC), for example. The wiring substrate F is accommodated in the housing 5. The wiring substrate F is coupled to the liquid crystal panel PNL in an area spaced apart from the optical system 2 in a cross direction d2. In comparison with the case where the wiring substrate F is coupled to the liquid crystal panel PNL in an area spaced apart from the optical system 2 in the diametrical direction d1, the one end surface S1 can be reduced, and furthermore, the main body 101 can be downsized.

For the connection between the wiring substrate F and the liquid crystal panel PNL, a thermocompression bonding method using an anisotropic conductive film (ACF) is used, for example. Using this method, an electrical connection between the plurality of pads of the liquid crystal panel PNL and the plurality of pads of the wiring substrate F is secured, and the wiring substrate F is fixed to the liquid crystal panel PNL. Note that the cross direction d2 is a direction that intersects the diametrical direction d1. In the present embodiment, the cross direction d2 is orthogonal to the diametrical direction d1. However, the cross direction d2 may also intersect the diametrical direction d1 at an angle other than 90°.

Here, the cross direction d2 is parallel to the direction X, and the diametrical direction d1 is parallel to the direction Y.

Figure 5:
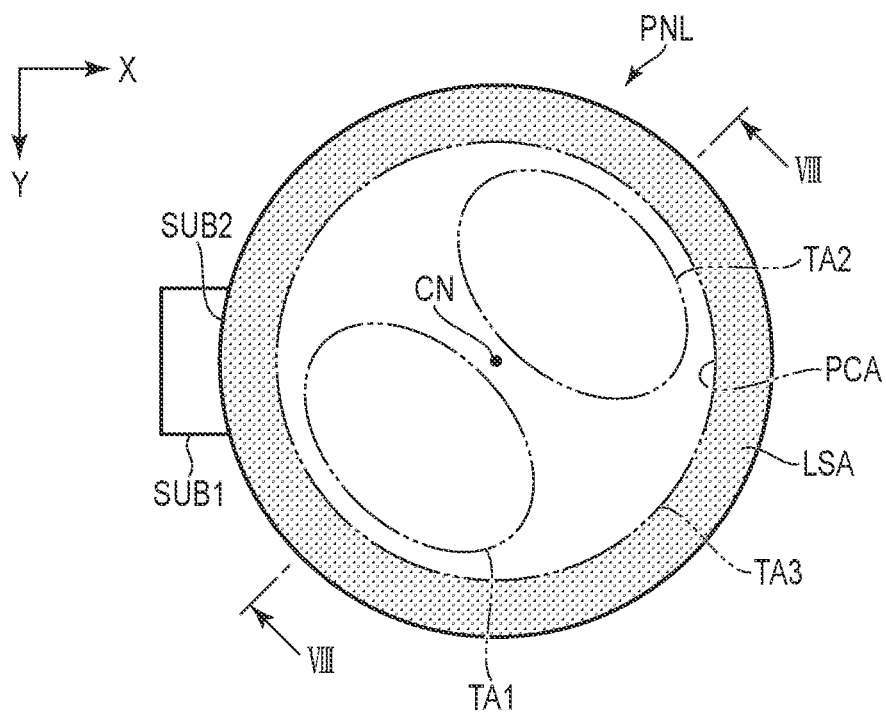
FIG. 5 is a plan view illustrating a liquid crystal panel illustrated in FIGS. 1, 3, and 4.

FIG. 5 is a plan view illustrating the liquid crystal panel PNL illustrated in FIGS. 1, 3, and 4. As illustrated in FIG. 5, the liquid crystal panel PNL has a first substrate SUB1 and a second substrate SUB2. The second substrate SUB2 has a circular shape. The first substrate SUB1 has a circular portion that completely overlaps the second substrate SUB2, and a protruding portion that protrudes from the circular portion and that does not overlap the second substrate SUB2.

In the area of overlap between the first substrate SUB1 and the second substrate SUB2, the liquid crystal panel PNL has an incident light control area PCA and a light shielding area LSA. The incident light control area PCA has a circular shape. The light shielding area LSA is located outside the incident light control area PCA and has a circular frame shape. In FIG. 5, a dot pattern has been added to the light shielding area LSA.

The incident light control area PCA has a first region TA1, a second region TA2 located so as to be shifted from the first region TA1, and a third region TA3 other than the first region TA1 and the second region TA2. The first region TA1 and the second region TA2 have an elliptical shape. However, the first region TA1 and the second region TA2 may have a perfect circle constituting a circular shape other than an ellipse, or a shape other than a circular shape.

The first region TA1 and the second region TA2 are the same in size (area) and shape. However, the first region TA1 and the second region TA2 may be different from each other in size and shape.

The first region TA1 and the second region TA2 are arranged side by side at intervals in a direction inclined counterclockwise by 45° from the direction X. The first region TA1 and the second region TA2 need not be arranged side by side in a direction inclined counterclockwise by 45° from the direction X. It is sufficient that the centroid of each of the first region TA1 and the second region TA2 be located so as to be shifted from the centroid CN of the incident light control area PCA, and the first region TA1 and the second region TA2 do not completely overlap each other. For this reason, the first region TA1 and the second region TA2 may be in contact with each other or may partially overlap each other. Note that the centroid CN of the incident light control area PCA is the center of the incident light control area PCA.

Figure 6:
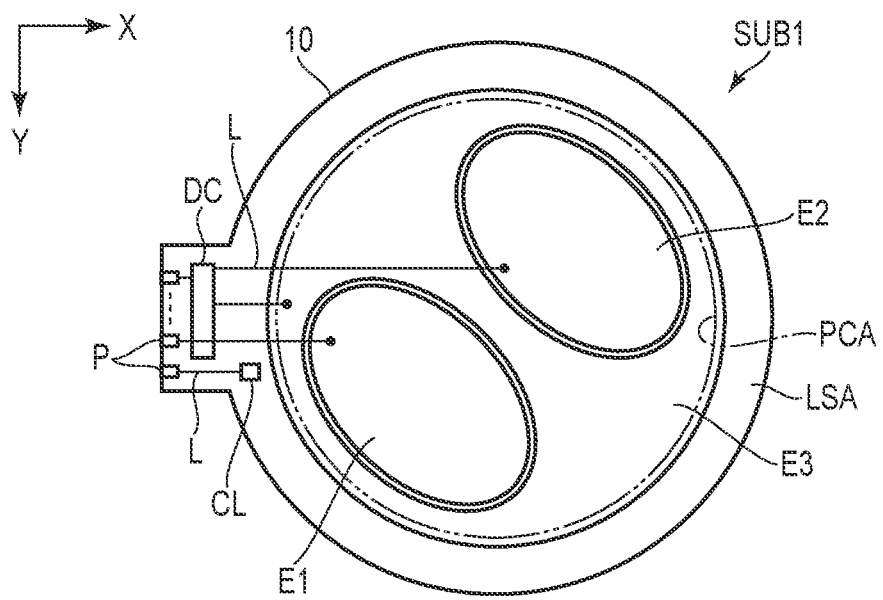
FIG. 6 is a plan view illustrating a first substrate and a driving circuit illustrated in FIG. 5.

FIG. 6 is a plan view illustrating the first substrate SUB1 and a driving circuit DC that are illustrated in FIG. 5. As illustrated in FIGS. 6 and 5, the first substrate SUB1 has a basement 10, a first electrode E1, a second electrode E2, a third electrode E3, a conductive layer CL, a plurality of wiring lines L, and a plurality of pads p of outer lead bonding (OLB). The first electrode E1 is located in the first region TA1; the second electrode E2 is located in the second region TA2; and the third electrode E3 is located in the third region TA3. The first electrode E1, the second electrode E2, and the third electrode E3 are provided at an insulation distance from each other. The third electrode E3 is provided across the boundary between the incident light control area PCA and the light shielding area LSA.

The conductive layer CL is located in the light shielding area LSA and is provided at an insulation distance from the third electrode E3. The plurality of pads p are provided above the basement 10 and are arranged side by side in an area not facing the second substrate SUB2. The driving circuit DC is mounted on the first substrate SUB1 and is located in an area not facing the second substrate SUB2. A plurality of wiring lines L connects each electrode E to the driving circuit DC, connects each pad p to the driving circuit DC, and connects the conductive layer CL to the pad p.

The driving circuit DC drives the first electrode E1, the second electrode E2, and the third electrode E3. Note that the driving circuit DC may be incorporated in the controlling circuit CC. In that case, each electrode E may be connected to the corresponding pad p via the wiring lines L.

Figure 7:
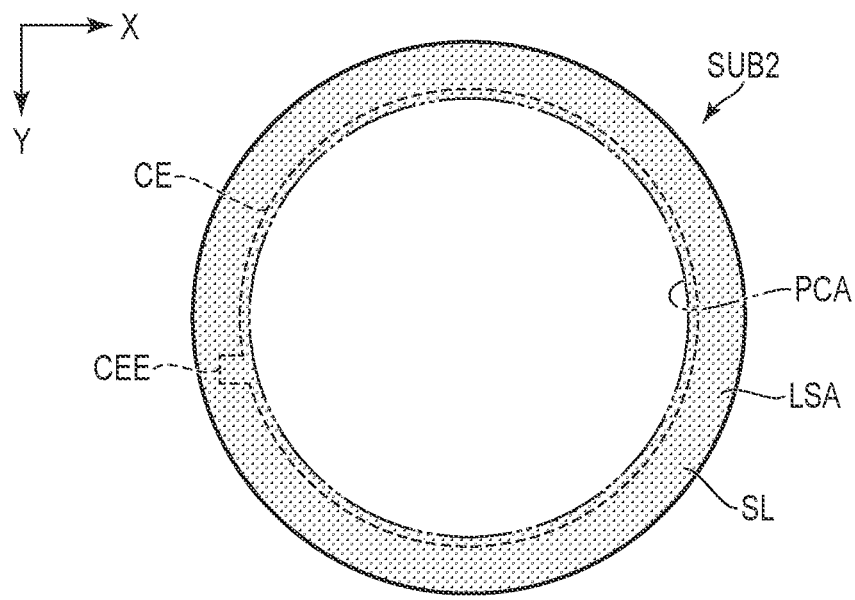
FIG. 7 is a plan view illustrating a second substrate illustrated in FIG. 5.

FIG. 7 is a plan view illustrating the second substrate SUB2 illustrated in FIG. 5. As illustrated in FIG. 7, the second substrate SUB2 has a basement 20, light shielding layer SL, and a counter-electrode CE. The counter-electrode CE is located in the incident light control area PCA. The counter-electrode CE is provided across the boundary between the incident light control area PCA and the light shielding area LSA.

The counter-electrode CE has a protruding portion CEE protruding toward the light shielding area LSA.

The protruding portion CEE overlaps the conductive layer CL of the first substrate SUB1 in plan view. The protruding portion CEE is electrically connected to the conductive layer CL via a conductive material (not illustrated). As a result, the controlling circuit CC is capable of applying a common voltage Vcom to the counter-electrode CE via the pad p, the wiring line L, the conductive layer CL, and the like.

The light shielding layer SL is located in the light shielding area LSA. The light shielding layer SL has an annular shape. The inner peripheral edge of the light shielding layer SL coincides with the outline of the incident light control area PCA. In the present embodiment, the light shielding layer is not provided in the incident light control area PCA. However, a light shielding layer may be provided at the boundary between the first electrode E1 and the third electrode E3 and the boundary between the second electrode E2 and the third electrode E3, respectively.

Figure 8:
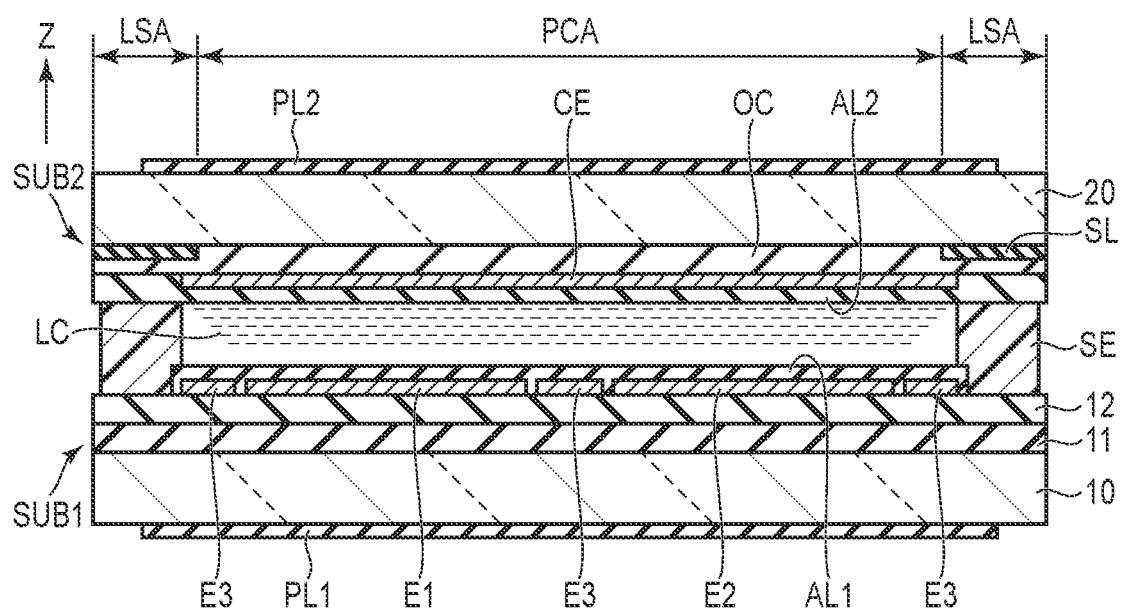
FIG. 8 is a cross-sectional view illustrating the liquid crystal panel taken along line VIII-VIII in FIG. 5.

FIG. 8 is a cross-sectional view illustrating the liquid crystal panel PNL taken along line VIII-VIII in FIG. 5. As illustrated in FIG. 8, the liquid crystal panel PNL includes a liquid crystal layer LC, a sealant SE, a polarizer PL1, and a polarizer PL2, in addition to the first substrate SUB1 and the second substrate SUB2. The liquid crystal panel PNL includes a configuration corresponding to a display mode that utilizes a vertical electric field along the normal line of the main surface of the substrate. Here, the main surface of the substrate is a surface parallel to the X-Y plane. Alternatively, the liquid crystal panel PNL may have any configuration corresponding to a display mode in which a lateral electric field along the main surface of the substrate is used, a display mode in which an inclined electric field inclined in an oblique direction with respect to the main surface of the substrate is used, and a display mode in which an appropriate combination of the lateral electric field, the vertical electric field, and the inclined electric field is used.

The sealant SE is located in the light shielding area LSA and bonds the first substrate SUB1 to the second substrate SUB2. The liquid crystal layer LC is located in the incident light control area PCA, and is held between the first substrate SUB1 and the second substrate SUB2. The liquid crystal layer LC is formed in a space surrounded by the first substrate SUB1, the second substrate SUB2, and the sealant SE.

The first substrate SUB1 further includes insulating layers 11 and 12, an alignment film AL1, and the like. The second substrate SUB2 faces the first substrate SUB1 in direction Z, is disposed at a gap from the first substrate SUB1, and further includes a transparent layer OC, an alignment film AL2, and the like. The basement 10 and the basement 20 are transparent substrates such as a glass substrate and a flexible resin substrate.

The insulating layer 11 is provided on the basement 10, and the insulating layer 12 is provided on the insulating layer 11. Note that the wiring lines L illustrated in FIG. 6 are located, for example, between the insulating layer 11 and the insulating layer 12. The first electrode E1, the second electrode E2, and the third electrode E3 are provided on the insulating layer 12. The first electrode E1, the second electrode E2, and the third electrode E3 are formed from a transparent conductive material such as indium tin oxide (ITO) or indium zinc oxide (IZO).

Note that the conductive layer (CL) illustrated in FIG. 6 is also formed of a transparent conductive material on the insulating layer 12, similarly to the first electrode E1 and the like. The alignment film AL1 is formed on the insulating layer 12, the first electrode E1, the second electrode E2, and the third electrode E3 and does not cover the conductive layer (CL).

In contrast, on the second substrate SUB2, the light shielding layer SL, the transparent layer OC, the counter-electrode CE, and the alignment film AL2 are sequentially formed on the first substrate SUB1 side of the basement 20. The counter-electrode CE is formed of a transparent conductive material such as ITO or IZO. The alignment film AL2 covers the counter-electrode CE. The alignment films AL1 and AL2 are in contact with the liquid crystal layer LC.

The polarizer PL1 and the polarizer PL2 are located at least in the incident light control area PCA, and sandwich the first substrate SUB1, the liquid crystal layer LC, and the second substrate SUB2. Note that the liquid crystal panel PNL may further include an optical sheet other than the polarizer PL1 and the polarizer PL2 in the incident light control area PCA.

The mode of the liquid crystal panel PNL is a so-called normally-black mode in which light is shielded in the OFF state.

In the incident light control area PCA, in a state where no voltage is applied between the electrodes E and the counter-electrode CE, the alignment axis (fast axis) of the liquid crystal molecules is orthogonal to or parallel to the transmission easy axis of the polarizer PL2 (or the polarizer PL1). For this reason, in a state where no voltage is applied to the liquid crystal layer LC, a retardation does not occur in the liquid crystal layer LC, and thus light is shielded because the transmission easy axes of the polarizer PL2 and the polarizer PL1 are orthogonal to each other (normally-black mode).

The mode of the liquid crystal panel PNL may also be a so-called normally-white mode in which light is shielded in the ON state (light is transmitted in the OFF state). In the incident light control area PCA, light is transmitted in a state where no voltage is applied across the electrodes E and the counter-electrode CE (normally-white mode).

Figure 9:
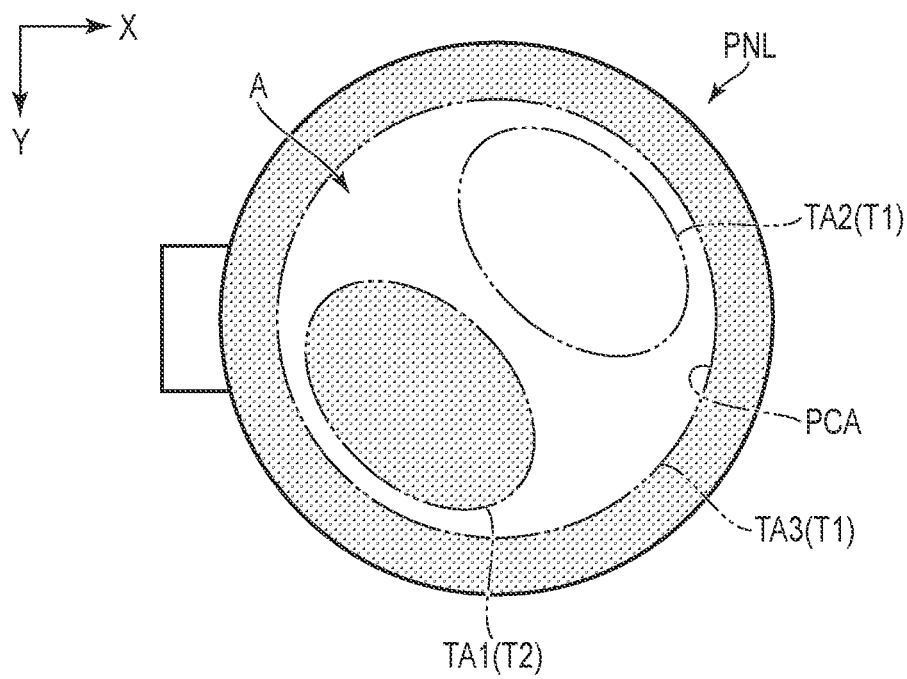
FIG. 9 is a plan view illustrating the liquid crystal panel, and is a view illustrating a state in which an incident light control area is set to a first light control pattern.
Figure 10:
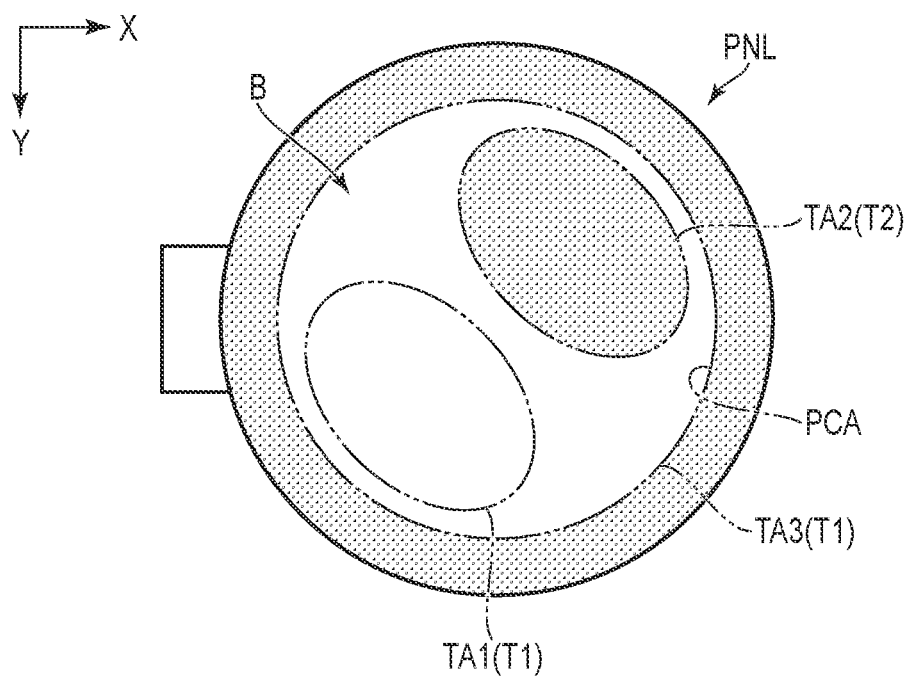
FIG. 10 is a plan view illustrating the liquid crystal panel, and is a view illustrating a state in which the incident light control area is set to a second light control pattern.

FIG. 9 is a plan view illustrating the liquid crystal panel PNL, and is a view illustrating a state in which the incident light control area PCA is set to a first light control pattern A. FIG. 10 is a plan view illustrating the liquid crystal panel PNL, and is a view illustrating a state in which the incident light control area PCA is set to a second light control pattern B.

In the incident light control area PCA of FIG. 9, a transmission region T1 is the second region TA2 and the third region TA3, and a non-transmission region T2 is the first region TA1.

In the incident light control area PCA of FIG. 10, the transmission region T1 is the first region TA1 and the third region TA3, and the non-transmission region T2 is the second region TA2.

As illustrated in FIGS. 9 and 10, the liquid crystal panel PNL is capable of alternately switching the incident light control area PCA between the first light control pattern A and the second light control pattern B. When switching to the first light control pattern A, the liquid crystal panel PNL sets the first region TA1 to the non-transmissive state, and sets the second region TA2 and the third region TA3, respectively, to the transmissive state. When switching to the second light control pattern B, the liquid crystal panel PNL sets the second region TA2 to the non-transmissive state, and sets the first region TA1 and the third region TA3, respectively, to the transmissive state. For this reason, a CAP (described subsequently) can be formed in the incident light control area PCA.

Here, the non-transmissive state refers to a light-shielding state in which visible light is shielded or a state in which transmittance is lower than that in the transmissive state.

As illustrated in FIGS. 9, 10, and 3, the controlling circuit CC acquires first image information acquired by performing first imaging of the subject by using the liquid crystal panel PNL with the first light control pattern A, and using the optical system 2, and the imaging element 3. Further, the controlling circuit CC acquires second image information acquired by performing second imaging of the subject by using the liquid crystal panel PNL with the second light control pattern B, and using the optical system 2, and the imaging element 3. As a result, the controlling circuit CC is capable of deriving an image of the subject and the distance from the imaging element 3 to the subject based on the first image information and the second image information.

In other words, the incident light control area PCA of FIG. 9 and the incident light control area PCA of FIG. 10 form coded aperture pair (CAP) that have mutually different patterns. For this reason, the camera 1 is capable of acquiring information about the light transmitted through the coded aperture of FIG. 9 and information about the light transmitted through the coded aperture of FIG. 10. The information about the light detected by the camera 1 includes information about the distance from the camera 1 (imaging element 3) to the subject. Thus, the controlling circuit CC is capable of deriving (measuring) the distance from the camera 1 to the subject based on the images (information) of two types (a plurality of types) captured by the camera 1.

Furthermore, the controlling circuit CC is capable of storing the image information about the subject and the data of the distance from the camera 1 to the subject, in the storage medium SM in association with each other.

The pattern of the coded aperture formed in the incident light control area PCA can be selected as appropriate so as to meet requirements regarding the distance from the camera 1 to the subject and regarding the resolution.

Furthermore, the liquid crystal panel PNL is also capable of switching the incident light control area PCA to a pattern other than the first light control pattern A and the second light control pattern B.

The liquid crystal panel PNL is capable of switching the incident light control area PCA to a light transmission pattern PTt or to a light shielding pattern PTs. When switching to the light transmission pattern PTt, the liquid crystal panel PNL sets all of the first region TA1, the second region TA2, and the third region TA3 to the transmissive state. When switching to the light shielding pattern PTs, the liquid crystal panel PNL sets all of the first region TA1, the second region TA2, and the third region TA3 to the non-transmissive state.

For example, the liquid crystal panel PNL is capable of switching the incident light control area PCA between the first light control pattern A, the second light control pattern B, and the light transmission pattern PTt. The controlling circuit CC is capable of acquiring image information about a subject using the camera 1 when the incident light control area PCA is switched to the light transmission pattern PTt, of acquiring distance data using the camera 1 when the incident light control area PCA is switched to the first light control pattern A and the second light control pattern B, and of associating the image information with the distance data.

The imaging device 100 according to the present embodiment is configured as described hereinabove.

Next, a plurality of driving methods by the controlling circuit CC according to the present embodiment will be described. Hereinafter, a first driving method, a second driving method, a third driving method, a fourth driving method, and a fifth driving method, which are some of a plurality of driving methods, will be described for illustrative purposes.

(First Driving Method)

Figure 11:
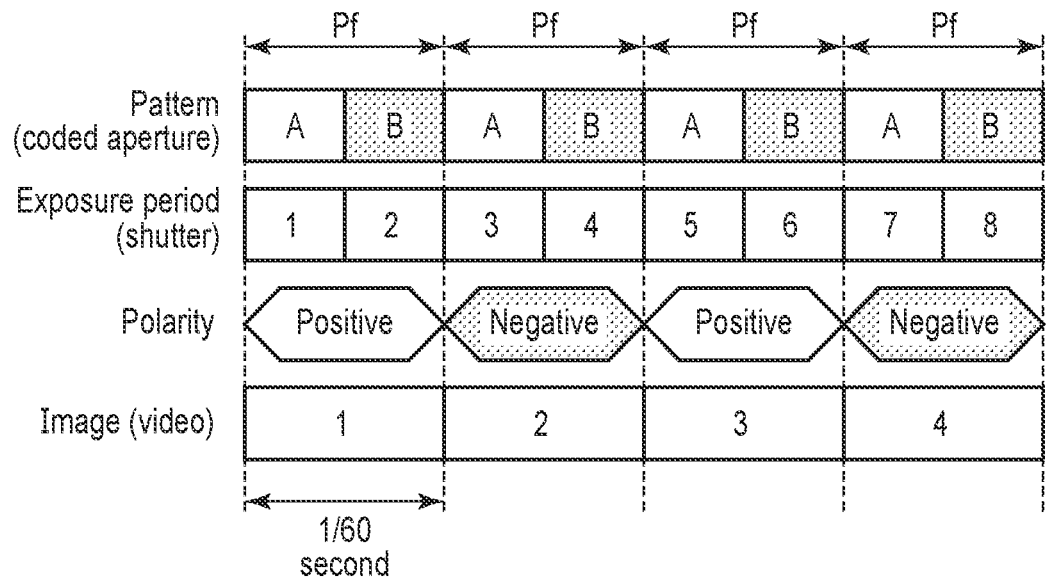
FIG. 11 is a diagram to illustrate a first driving method by a controlling circuit of the imaging device according to the first embodiment, and is a timing chart illustrating patterns that are set in the incident light control area, exposure periods of a camera of the imaging device, polarities of voltages applied to a plurality of electrodes of the first substrate, and images derived by the controlling circuit.

First, a first driving method will be described. FIG. 11 is a diagram to illustrate a first driving method by the controlling circuit CC of the imaging device 100 according to the present embodiment, and is a timing chart illustrating patterns that are set in the incident light control area PCA, exposure periods of the camera 1, polarities of voltages to be applied to a plurality of electrodes E of the first substrate SUB1, and images derived by the controlling circuit CC.

As illustrated in FIG. 11, one frame period Pf is the period required to derive the distance from the camera 1 (imaging element 3) to the subject. In the first driving method, one frame period Pf is 1/60 second, and is a period in which one imaging is performed by switching the incident light control area PCA to the first light control pattern A and one imaging is performed by switching the incident light control area PCA to the second light control pattern B.

In association with the pattern of the incident light control area PCA, the controlling circuit CC adjusts the period during which the shutter of the camera 1 is opened (the exposure period of the camera 1). The controlling circuit CC opens the shutter of the camera 1 in a period in which the incident light control area PCA is switched to the first light control pattern A, and re-opens the shutter of the camera 1 in a period in which the incident light control area PCA is switched to the second light control pattern B.

The exposure period of the camera 1 corresponding to each pattern of the incident light control area PCA is substantially 1/120 second, and the period during which light is captured by the imaging element 3 can be made longer than in the 1/240 second case.

The controlling circuit CC is capable of deriving the distance from the camera 1 to the subject in one frame period Pf, and also of deriving one image of the subject.

By applying this first driving method to a plurality of consecutive frame periods Pf, it is possible to obtain a change in the distance from the camera 1 to the subject and a change in the subject (imaging target). For this reason, the controlling circuit CC is capable of obtaining a video of the subject together with the distance information.

The controlling circuit CC applies the common voltage Vcom to the counter-electrode CE. The driving circuit DC supplies a control signal to the first electrode E1, the second electrode E2, and the third electrode E3, respectively. The driving circuit DC performs polarity inversion driving by taking, as targets, at least the first electrode E1 and the second electrode E2. The polarity of the control signal supplied to at least the first electrode E1 and the second electrode E2 is inverted for each one frame period Pf.

When the mode of the liquid crystal panel PNL is the normally black mode, the driving circuit DC performs the polarity inversion driving by taking, as targets, all of the first electrode E1, the second electrode E2, and the third electrode E3. Here, a control signal of a voltage level which is positive with respect to the common voltage Vcom is referred to as a positive-polarity control signal, a control signal of a voltage level which is negative with respect to the common voltage Vcom is referred to as a negative-polarity control signal, and a control signal which has the same voltage level as the common voltage Vcom is referred to as a reference control signal.

The driving circuit DC is capable of repeatedly performing driving according to the following items (1) to (4) performed in two consecutive frame periods.

(1) The driving circuit DC supplies the reference control signal to the first electrode E1, and supplies a positive-polarity control signal to the second electrode E2 and the third electrode E3. The driving circuit DC is capable of outputting a positive-polarity control signal or the like, and of setting the incident light control area PCA to the first light control pattern A.

(2) Thereafter, the driving circuit DC supplies the reference control signal to the second electrode E2, and supplies a positive-polarity control signal to the first electrode E1 and the third electrode E3. The driving circuit DC is capable of outputting a positive-polarity control signal or the like, and of switching the incident light control area PCA to the second light control pattern B.

(3) Thereafter, the driving circuit DC supplies the reference control signal to the first electrode E1, and supplies a negative-polarity control signal to the second electrode E2 and the third electrode E3. The driving circuit DC is capable of outputting a negative-polarity control signal or the like, and of switching the incident light control area PCA to the first light control pattern A.

(4) Thereafter, the driving circuit DC supplies the reference control signal to the second electrode E2, and supplies a negative-polarity control signal to the first electrode E1 and the third electrode E3. The driving circuit DC is capable of outputting a negative-polarity control signal or the like, and of switching the incident light control area PCA to the second light control pattern B.

In the embodiment of the first driving method, although one frame period Pf is set to 1/60 second, one frame period Pf may be set to 1/120 second or 1/240 second.

(Second Driving Method)

Figure 12:
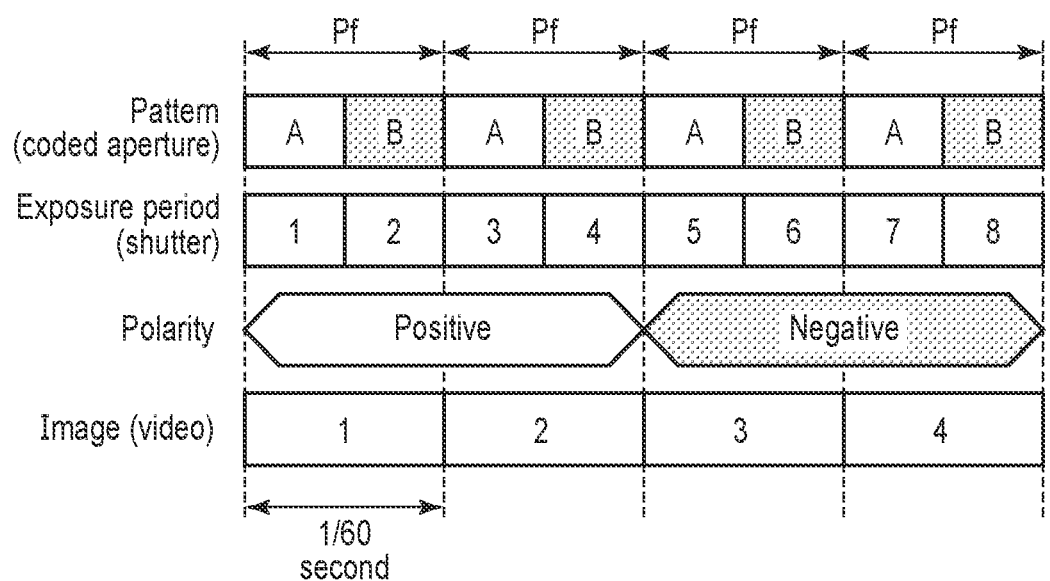
FIG. 12 is a diagram to illustrate a second driving method by the controlling circuit of the imaging device according to the first embodiment, and is a timing chart illustrating the patterns, the exposure periods, the polarities, and the images.

Next, a second driving method will be described. FIG. 12 is a diagram to illustrate the second driving method by the controlling circuit CC of the imaging device 100 according to the present embodiment, and is a timing chart illustrating patterns that are set in the incident light control area PCA, exposure periods of the camera 1, polarities of voltages to be applied to a plurality of electrodes E of the first substrate SUB1, and images derived by the controlling circuit CC.

As illustrated in FIG. 12, the second driving method is different from the first driving method in that the polarity of the control signal supplied to at least the first electrode E1 and the second electrode E2 is inverted every two frame periods.

(Third Driving Method)

Figure 13:
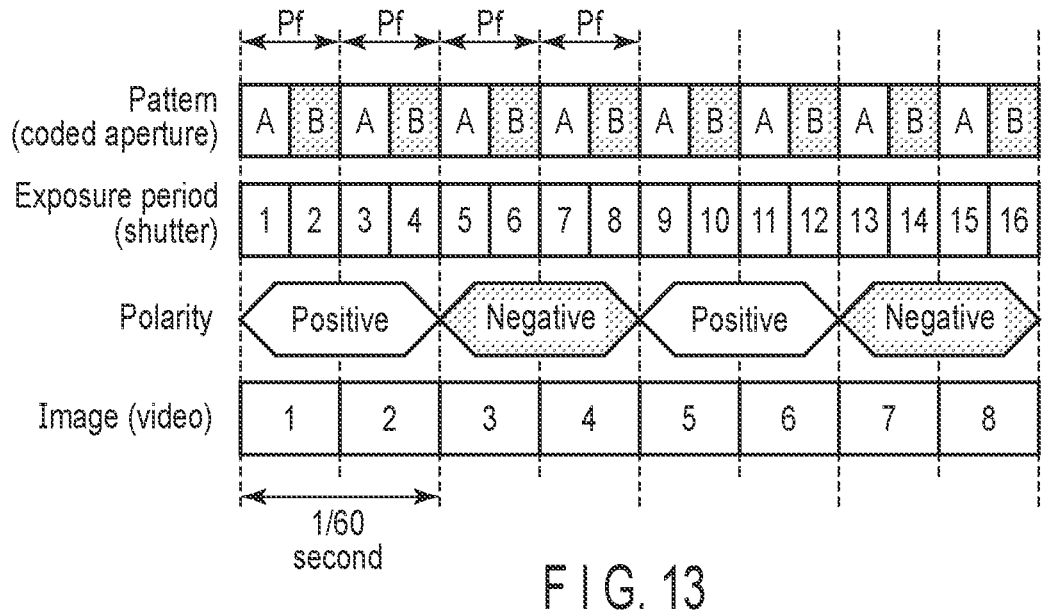
FIG. 13 is a diagram to illustrate a third driving method by the controlling circuit of the imaging device according to the first embodiment, and is a timing chart illustrating the patterns, the exposure periods, the polarities, and the images.

Next, a third driving method will be described. FIG. 13 is a diagram to illustrate the third driving method by the controlling circuit CC of the imaging device 100 according to the present embodiment, and is a timing chart illustrating patterns that are set in the incident light control area PCA, exposure periods of the camera 1, polarities of voltages to be applied to a plurality of electrodes E of the first substrate SUB1, and images derived by the controlling circuit CC.

As illustrated in FIG. 13, the third driving method is different from the first driving method in that one frame period Pf is 1/120 second. The exposure period of the camera 1 corresponding to each pattern of the incident light control area PCA is substantially 1/240 second, and the period during which light is captured by the imaging element 3 can be made shorter than in the 1/120 second case.

The imaging device 100 is capable of imaging a subject at a high frame rate. The imaging device 100 is capable of obtaining the frame rate required for a period in which the subject (imaging target) changes due to a forward action or a backward action of the imaging device 100 (main body 101), or a period in which forceps are operated, or the like. If insufficient exposure occurs in the camera 1 (imaging element 3), the illuminance of the illumination device EM may be increased to illuminate the subject. Thus, it is possible to compensate for insufficient exposure in the camera 1.

(Fourth Driving Method)

Figure 14A:
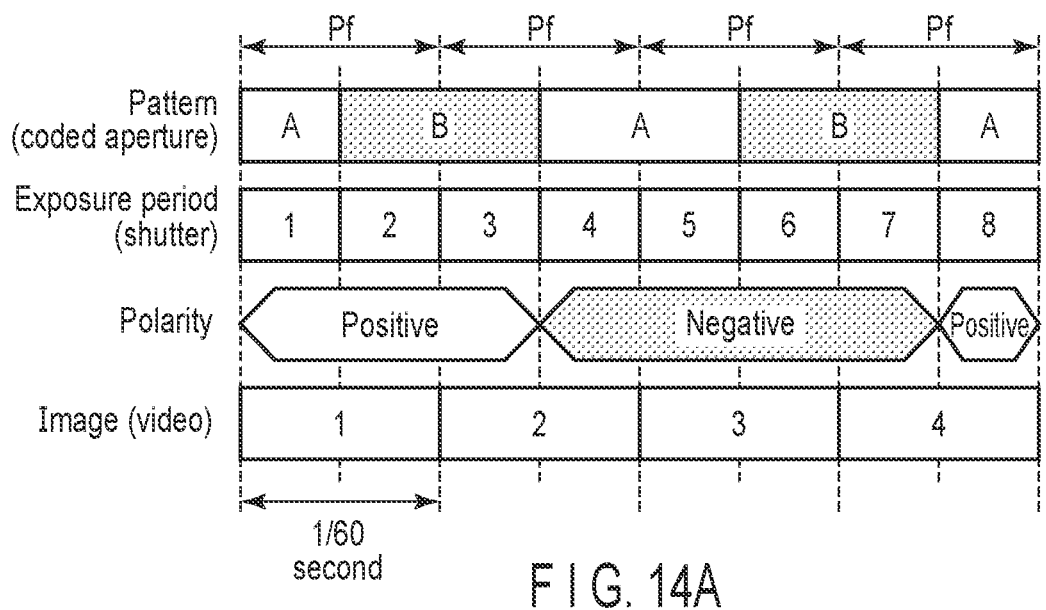
FIG. 14A is a diagram to illustrate a fourth driving method by the controlling circuit of the imaging device according to the first embodiment, and is a timing chart illustrating the patterns, the exposure periods, the polarities, and the images.

Next, a fourth driving method will be described. FIG. 14A is a diagram to illustrate the fourth driving method by the controlling circuit CC of the imaging device 100 according to the present embodiment, and is a timing chart illustrating patterns that are set in the incident light control area PCA, exposure periods of the camera 1, polarities of voltages to be applied to a plurality of electrodes E of the first substrate SUB1, and images derived by the controlling circuit CC.

As illustrated in FIG. 14A, the fourth driving method is different from the first driving method in that the incident light control area PCA is switched between the first light control pattern A and the second light control pattern B every 1/60 second, and in that the polarity of the control signal supplied to at least the first electrode E1 and the second electrode E2 is inverted every 1/30 second.

When the incident light control area PCA is switched to the second light control pattern B in the latter half of an arbitrary one frame period Pf, the incident light control area PCA may be held in the second light control pattern B in the first half of the subsequent one frame period Pf.

((4-1)Th Driving Method)

Figure 14B:
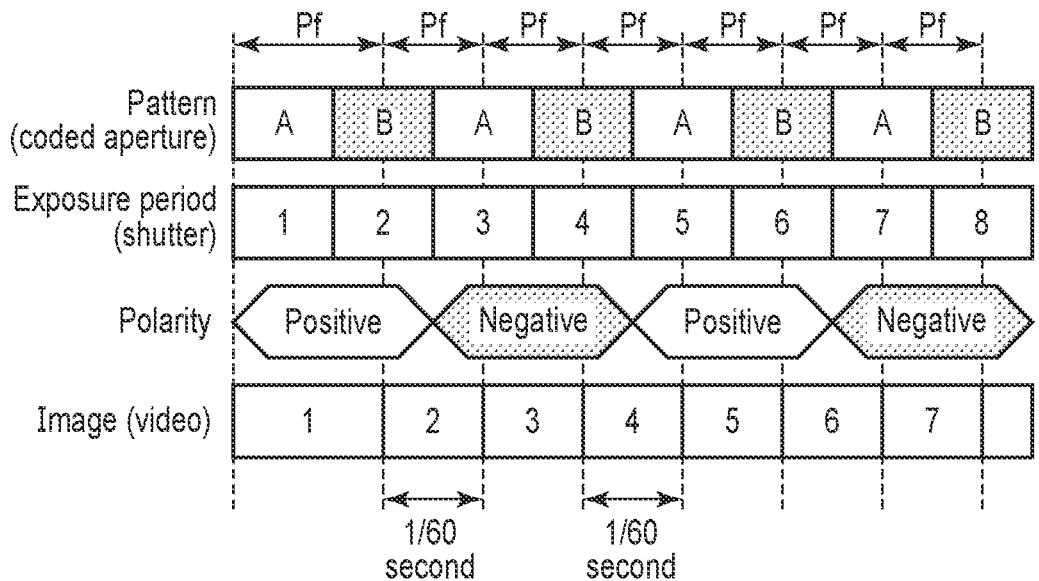
FIG. 14B is a diagram to illustrate a (4-1)th driving method by the controlling circuit of the imaging device according to the first embodiment, and is a timing chart illustrating the patterns, the exposure periods, the polarities, and the images.

Next, a (4-1)th driving method will be described. FIG. 14B is a diagram to illustrate the (4-1)th driving method by the controlling circuit CC of the imaging device 100 according to the present embodiment, and is a timing chart illustrating patterns that are set in the incident light control area PCA, exposure periods of the camera 1, polarities of voltages to be applied to a plurality of electrodes E of the first substrate SUB1, and images derived by the controlling circuit CC. As illustrated in FIG. 14B, the (4-1)th driving method is different from the fourth driving method in that the incident light control area PCA is switched between the first light control pattern A and the second light control pattern B every 1/120 second, and in that the polarity of the control signal supplied to at least the first electrode E1 and the second electrode E2 is inverted every 1/60 second. When the incident light control area PCA is switched to either the first light control pattern A or the second light control pattern B, the (4-1)th driving method is different from the fourth driving method in that the exposure of the camera is performed once each time.

When the incident light control area PCA is switched to the second light control pattern B in the latter half of an arbitrary one frame period Pf, the incident light control area PCA may be held in the second light control pattern B in the first half of the subsequent one frame period Pf.

(Fifth Driving Method)

Figure 15:
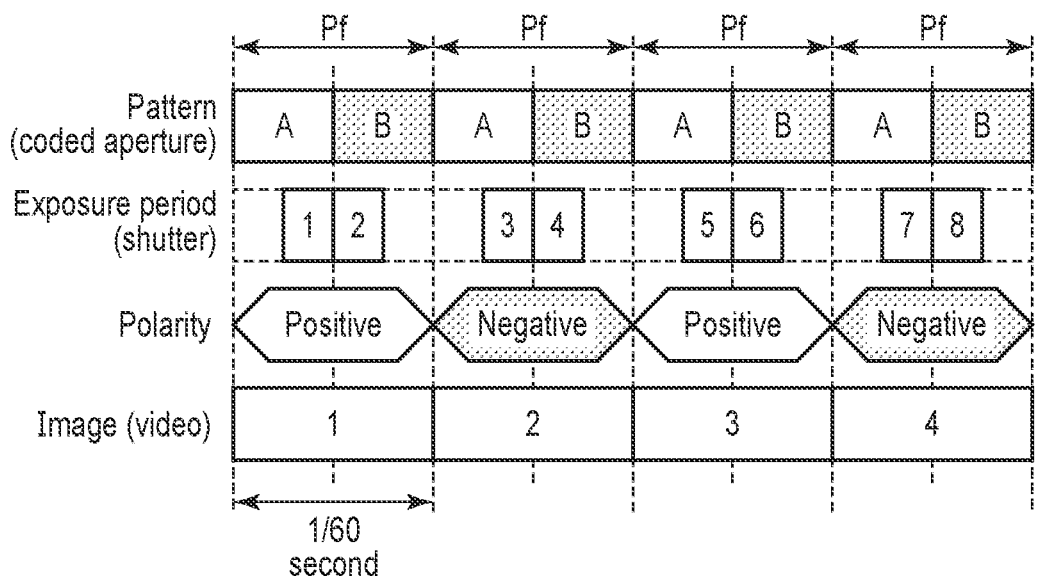
FIG. 15 is a diagram to illustrate a fifth driving method by the controlling circuit of the imaging device according to the first embodiment, and is a timing chart illustrating the patterns, the exposure periods, the polarities, and the images.

Next, a fifth driving method will be described. FIG. 15 is a diagram to illustrate the fifth driving method by the controlling circuit CC of the imaging device 100 according to the present embodiment, and is a timing chart illustrating patterns that are set in the incident light control area PCA, exposure periods of the camera 1, polarities of voltages to be applied to a plurality of electrodes E of the first substrate SUB1, and images derived by the controlling circuit CC.

As illustrated in FIG. 15, the fifth driving method is different from the first driving method in that, in each one frame period Pf, the exposure period of the camera 1 corresponding to each pattern of the incident light control area PCA is shorter than 1/120 second, and the exposure interval (imaging interval) is narrow.

Even if the subject is imaged during a period in which a forward action or a backward action of the imaging device 100 (main body 101) is performed, the captured image is hardly blurred. For this reason, the controlling circuit CC is capable of obtaining a detailed video of the subject together with precise information relating to distance.

In the imaging device 100 according to the first embodiment configured as described above, the imaging device 100 includes the liquid crystal panel PNL, which is capable of forming the CAP. For this reason, even if the imaging device 100 includes a single camera 1, the distance from the imaging element 3 to the subject can be measured by combining the camera 1 with the liquid crystal panel PNL, and the imaging device 100 is capable of capturing a stereoscopic image or a stereoscopic video of the subject. For this reason, it is possible to obtain an imaging device 100 which is capable of capturing a stereoscopic image by using a monocular camera.

Furthermore, in order to capture a stereoscopic image or a stereoscopic video, the imaging device 100 need not include a compound-eye camera. In comparison with a case where the imaging device 100 includes a compound-eye camera, it is possible to obtain an imaging device 100 in which the main body 101, and hence the imaging device 100, is downsized.

Second Embodiment

Figure 16:
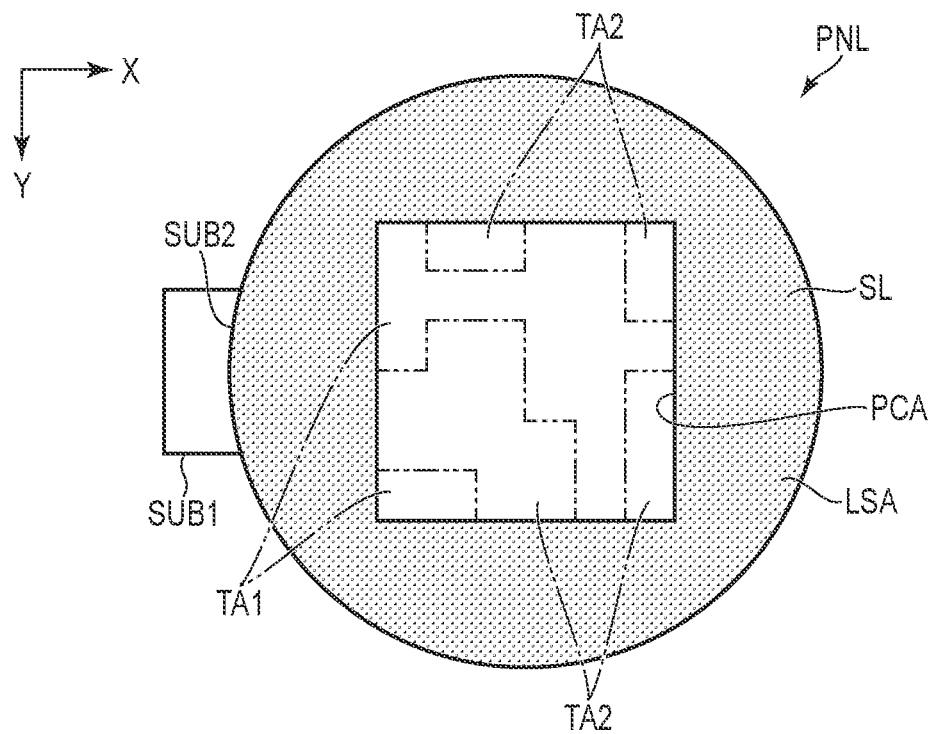
FIG. 16 is a plan view illustrating a liquid crystal panel of an imaging device according to a second embodiment.

A second embodiment will be described next. An imaging device 100 is configured similarly to that of the first embodiment except for the configuration described in the second embodiment. FIG. 16 is a plan view illustrating a liquid crystal panel PNL of an imaging device 100 according to the present embodiment. In FIG. 16, a dot pattern has been added to the light shielding area LSA.

As illustrated in FIG. 16, the configuration of the liquid crystal panel PNL is different from the configuration of the liquid crystal panel of the first embodiment. The incident light control area PCA includes a plurality of first regions TA1 that are located in a dispersed manner in the incident light control area PCA, and a plurality of second regions TA2 other than the plurality of first regions TA1 in the incident light control area PCA. The plurality of second regions TA2 are not concentrated in the incident light control area PCA. The plurality of first regions TA1 and the plurality of second regions TA2 form a specific pattern. The incident light control area PCA has a quadrangular shape, but may have a shape other than the quadrangular shape, such as a circular shape.

Figure 17:
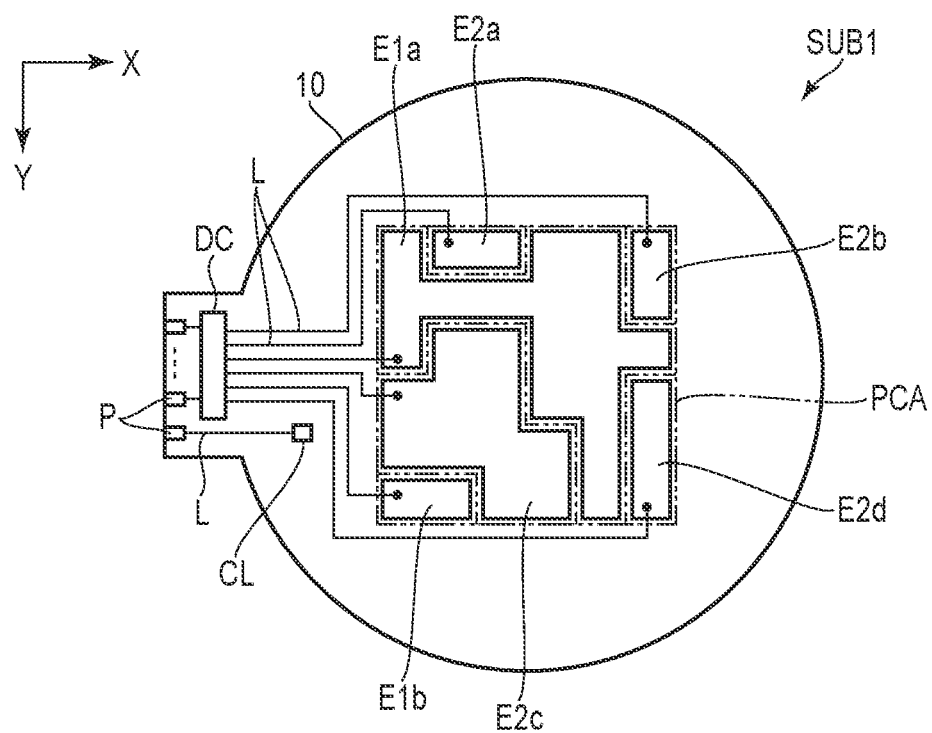
FIG. 17 is a plan view illustrating the first substrate and the driving circuit illustrated in FIG. 16.

FIG. 17 is a plan view illustrating a first substrate SUB1 and a driving circuit DC that are illustrated in FIG. 16. As illustrated in FIGS. 17 and 16, the first substrate SUB1 has a basement 10, a plurality of first electrodes E1a and E1b, a plurality of second electrodes E2a, E2b, E2c, and E2d, a conductive layer CL, a plurality of wiring lines L, and a plurality of pads p of outer lead bonding (OLB).

Each of the first electrodes E1a and E1b is located in a corresponding one first region TA1 among the plurality of first regions TA1. Each of the second electrodes E2a, E2b, E2c, and E2d is located in a corresponding one second region TA2 among the plurality of second regions TA2. The first electrodes E1a and E1b, and the second electrodes E2a, E2b, E2c, and E2d are provided at an insulation distance from each other. A plurality of wiring lines L connects each electrode E to the driving circuit DC, connects each pad p to the driving circuit DC, and connects the conductive layer CL to the pad p.

The driving circuit DC drives the plurality of first electrodes E1a and E1b and the plurality of second electrodes E1a, E2b, E1c, and E2d. In the present embodiment, the driving circuit DC may be incorporated in the controlling circuit CC. In that case, each electrode E may be connected to the corresponding pad p via the wiring line L.

Figure 18:
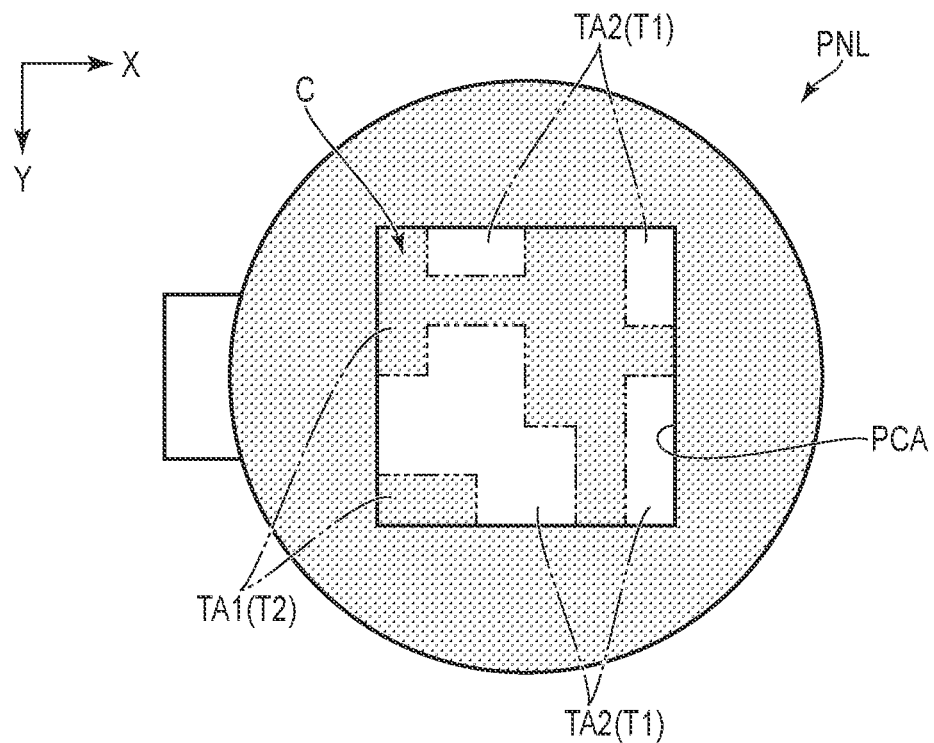
FIG. 18 is a plan view illustrating the liquid crystal panel according to the second embodiment, and is a view illustrating a state in which an incident light control area is set to a light control pattern.

FIG. 18 is a plan view illustrating the liquid crystal panel PNL according to the present embodiment, and is a view illustrating a state in which the incident light control area PCA is set to a light control pattern C.

As illustrated in FIG. 18, the liquid crystal panel PNL switches the incident light control area PCA to the light control pattern C. When switching to the light control pattern C, the liquid crystal panel PNL sets each of the plurality of first regions TA1 to the non-transmissive state, and sets each of the second regions TA2 to the transmissive state. The transmission region T1 is a plurality of second regions TA2, and the non-transmission region T2 is a plurality of first regions TA1. For this reason, a coded aperture (CA) can be formed in the incident light control area PCA.

As illustrated in FIGS. 18 and 3, the controlling circuit CC acquires image information acquired by performing imaging of the subject by using the liquid crystal panel PNL with the light control pattern C, and using the optical system 2, and the imaging element 3. As a result, the controlling circuit CC is capable of deriving an image of the subject and the distance from the imaging element 3 to the subject based on the image information.

In other words, the camera 1 acquires information about the light transmitted through the incident light control area PCA illustrated in FIG. 18. By using the specific pattern illustrated in FIG. 18, for example, the controlling circuit CC described above is capable of deriving the distance from the camera 1 (imaging element 3) to the subject based on one type of information acquired by the camera 1.

Furthermore, the controlling circuit CC is capable of storing the image information about the subject and the data of the distance from the camera 1 to the subject, in the storage medium SM in association with each other.

The pattern of the coded aperture formed in the incident light control area PCA can be selected as appropriate so as to meet requirements regarding the distance from the camera 1 to the subject and regarding the resolution.

Furthermore, the liquid crystal panel PNL is also capable of switching the incident light control area PCA to a pattern other than the light control pattern C.

The liquid crystal panel PNL is capable of switching the incident light control area PCA to a light transmission pattern PTt or to a light shielding pattern PTs. When switching to the light transmission pattern PTt, the liquid crystal panel PNL sets all of the plurality of first regions TA1 and the plurality of second regions TA2 to the transmissive state. When switching to the light shielding pattern PTs, the liquid crystal panel PNL sets all of the plurality of first regions TA1 and the plurality of second regions TA2 to the non-transmissive state.

For example, the liquid crystal panel PNL is capable of switching the incident light control area PCA between the light control pattern C and the light transmission pattern PTt. The controlling circuit CC is capable of acquiring image information about a subject by using the camera 1 when the incident light control area PCA is switched to the light transmission pattern PTt, of acquiring distance data using the camera 1 when the incident light control area PCA is switched to the light control pattern C, and of associating the image information with the distance data.

The imaging device 100 according to the present embodiment is configured as described hereinabove.

Next, a plurality of driving methods by the controlling circuit CC according to the present embodiment will be described. Hereinafter, a first driving method, a second driving method, and a third driving method, which are some of a plurality of driving methods, will be described for illustrative purposes.

(First Driving Method)

Figure 19:
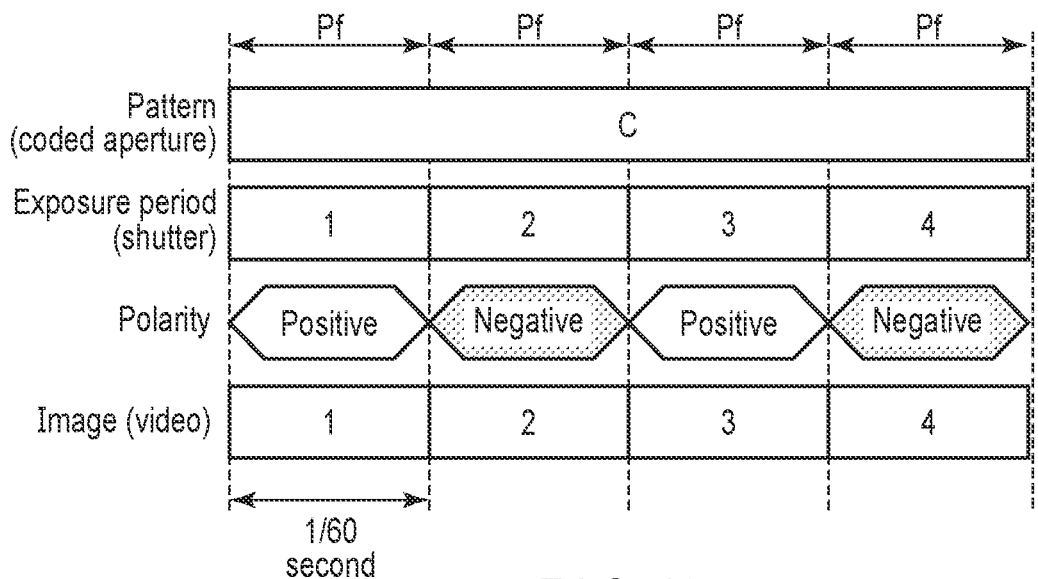
FIG. 19 is a diagram to illustrate a first driving method by a controlling circuit of the imaging device according to the second embodiment, and is a timing chart illustrating patterns that are set in the incident light control area, exposure periods of a camera of the imaging device, polarities of voltages applied to a plurality of electrodes of the first substrate, and images derived by the controlling circuit.

First, a first driving method will be described. FIG. 19 is a diagram to illustrate the first driving method by the controlling circuit CC of the imaging device 100 according to the present embodiment, and is a timing chart illustrating patterns that are set in the incident light control area PCA, exposure periods of the camera 1, polarities of voltages to be applied to a plurality of electrodes E of the first substrate SUB1, and images derived by the controlling circuit CC.

As illustrated in FIG. 19, one frame period Pf is the period required to derive the distance from the camera 1 (imaging element 3) to the subject. In the first driving method, one frame period Pf is $\frac{1}{60}$ second, and is a period in which one imaging is performed by switching the incident light control area PCA to the light control pattern C.

In association with each one frame period Pf, the controlling circuit CC adjusts the period during which the shutter of the camera 1 is opened (the exposure period of the camera 1). The controlling circuit CC opens the shutter of the camera 1 in an arbitrary one frame period Pf, and re-opens the shutter of the camera 1 when shifting to another subsequent one frame period Pf.

The exposure period of the camera 1 corresponding to each one frame period Pf is substantially $\frac{1}{60}$ second, and the period during which light is captured by the imaging element 3 can be made longer than in the $\frac{1}{120}$ second case.

The controlling circuit CC is capable of deriving the distance from the camera 1 to the subject in one frame period Pf, and also of deriving one image of the subject.

By applying this first driving method to a plurality of consecutive frame periods Pf, it is possible to obtain a change in the distance from the camera 1 to the subject and a change in the subject (imaging target). For this reason, the controlling circuit CC is capable of obtaining a video of the subject together with the distance information.

The controlling circuit CC applies the common voltage Vcom to the counter-electrode CE. The driving circuit DC supplies a control signal to the plurality of first electrodes E1a and E1b and the plurality of second electrodes Eta, E2b, Etc, and E2d, respectively.

The driving circuit DC performs polarity inversion driving by taking, as targets, one plurality of electrodes among the plurality of first electrodes E1a and E1b and the plurality of second electrodes E2a, E2b, E2c, and E2d. The polarities of the control signals supplied to one plurality of electrodes among at least the plurality of first electrodes E1a and E1b and the plurality of second electrodes E2a, E2b, E2c, and E2d are inverted every one frame period Pf. When the mode of the liquid crystal panel PNL is the normally black mode, the driving circuit DC performs the polarity inversion driving by taking, as targets, the plurality of second electrodes E2a, E2b, E2c, and E2d.

The driving circuit DC is capable of repeatedly performing driving according to the following items (1) and (2) performed in two consecutive frame periods.

(1) The driving circuit DC supplies a reference control signal to the plurality of first electrodes E1a and E1b and supplies a positive-polarity control signal to the plurality of second electrodes E2a, E2b, E2c, and E2d. The driving circuit DC is capable of outputting a positive-polarity control signal or the like, and of setting the incident light control area PCA to the light control pattern C.

(2) Thereafter, the driving circuit DC supplies a reference control signal continuously to the plurality of first electrodes E1a and E1b and supplies a negative-polarity control signal to the plurality of second electrodes E2a, E2b, E2c, and E2d. The driving circuit DC is capable of outputting a negative-polarity control signal or the like, and of holding the incident light control area PCA in a state of being set to the light control pattern C.

The coded aperture formed in the incident light control area PCA is one type of light control pattern C. There is no need to switch between the plurality of coded apertures. For this reason, a reduction in the power consumption can be achieved. Furthermore, the controlling circuit CC is capable of deriving the distance from the camera 1 to the subject based on one type of image information acquired using the light control pattern C. The distance can be quickly derived in comparison with a case where the distance is derived based on a plurality of types of image information.

In the embodiment of the first driving method, although one frame period Pf is set to 1/60 second, one frame period Pf may be set to 1/120 second or 1/240 second.

(Second Driving Method)

Figure 20:
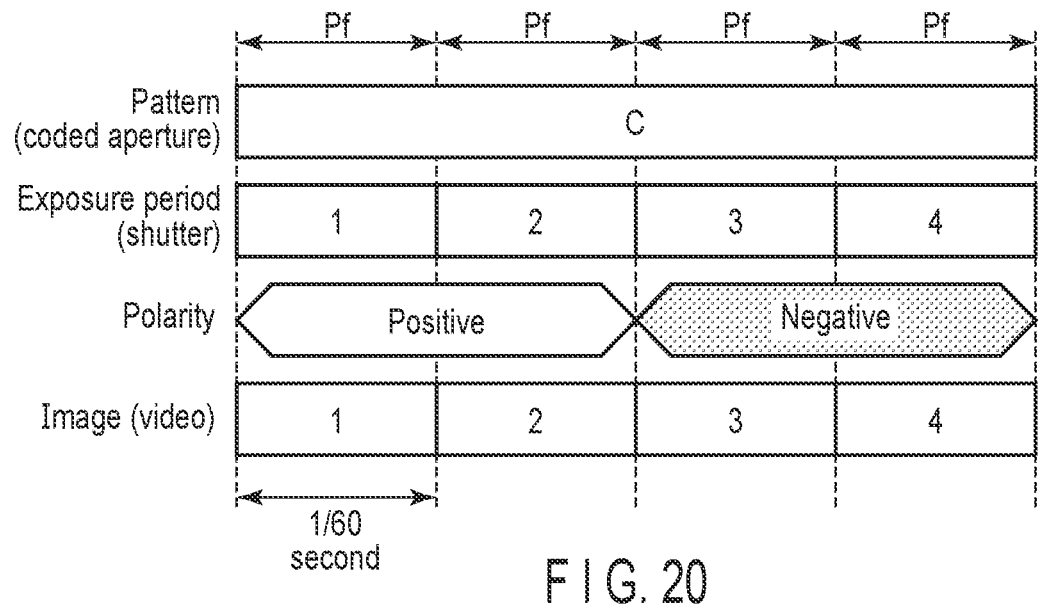
FIG. 20 is a diagram to illustrate a second driving method by a controlling circuit of the imaging device according to the second embodiment, and is a timing chart illustrating patterns that are set in the incident light control area, exposure periods of a camera of the imaging device, polarities of voltages applied to a plurality of electrodes of the first substrate, and images derived by the controlling circuit.

Next, a second driving method will be described. FIG. 20 is a diagram to illustrate the second driving method by the controlling circuit CC of the imaging device 100 according to the present embodiment, and is a timing chart illustrating patterns that are set in the incident light control area PCA, exposure periods of the camera 1, polarities of voltages to be applied to a plurality of electrodes E of the first substrate SUB1, and images derived by the controlling circuit CC.

As illustrated in FIG. 20, the second driving method is different from the first driving method in that the polarity of the control signal supplied to the plurality of second electrodes E2a, E2b, E2c, and E2d is inverted every two frame periods.

(Third Driving Method)

Figure 21:
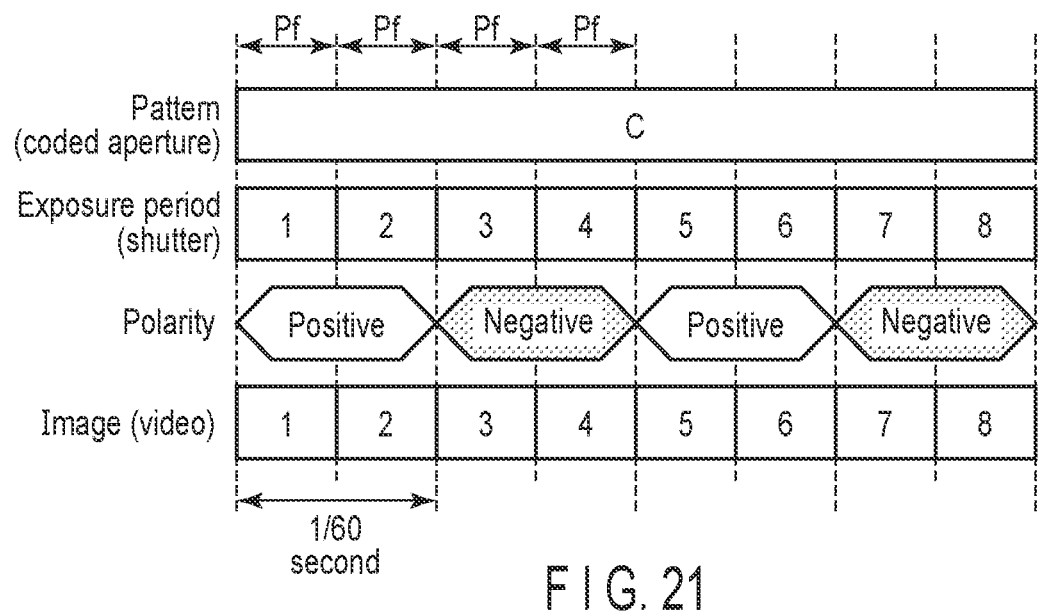
FIG. 21 is a diagram to illustrate a third driving method by a controlling circuit of the imaging device according to the second embodiment, and is a timing chart illustrating patterns that are set in the incident light control area, exposure periods of a camera of the imaging device, polarities of voltages applied to a plurality of electrodes of the first substrate, and images derived by the controlling circuit.

Next, a third driving method will be described. FIG. 21 is a diagram to illustrate the third driving method by the controlling circuit CC of the imaging device 100 according to the present embodiment, and is a timing chart illustrating patterns that are set in the incident light control area PCA, exposure periods of the camera 1, polarities of voltages to be applied to a plurality of electrodes E of the first substrate SUB1, and images derived by the controlling circuit CC.

As illustrated in FIG. 21, the third driving method is different from the first driving method in that one frame period Pf is 1/120 second. The exposure period of the camera 1 corresponding to each pattern of the incident light control area PCA is substantially 1/120 second, and the period during which light is captured by the imaging element 3 can be made shorter than in the 1/60 second case.

The imaging device 100 is capable of imaging a subject at a high frame rate. The imaging device 100 is capable of obtaining the frame rate required for a period in which the subject (imaging target) changes due to a forward action or a backward action of the imaging device 100 (main body 101), or a period in which forceps are operated, or the like. If insufficient exposure occurs in the camera 1 (imaging element 3), the illuminance of the illumination device EM may be increased to illuminate the subject.

In the imaging device 100 according to the second embodiment configured as described above, the imaging device 100 includes the liquid crystal panel PNL, which is capable of forming the CA. For this reason, even if the imaging device 100 includes a single camera 1, the distance from the imaging element 3 to the subject can be measured by combining the camera 1 with the liquid crystal panel PNL, and the imaging device 100 is capable of capturing a stereoscopic image or a stereoscopic video of the subject. For this reason, the second embodiment is capable of obtaining the same advantageous effects as those of the first embodiment described above.

One Modified Example of Second Embodiment

Figure 22:
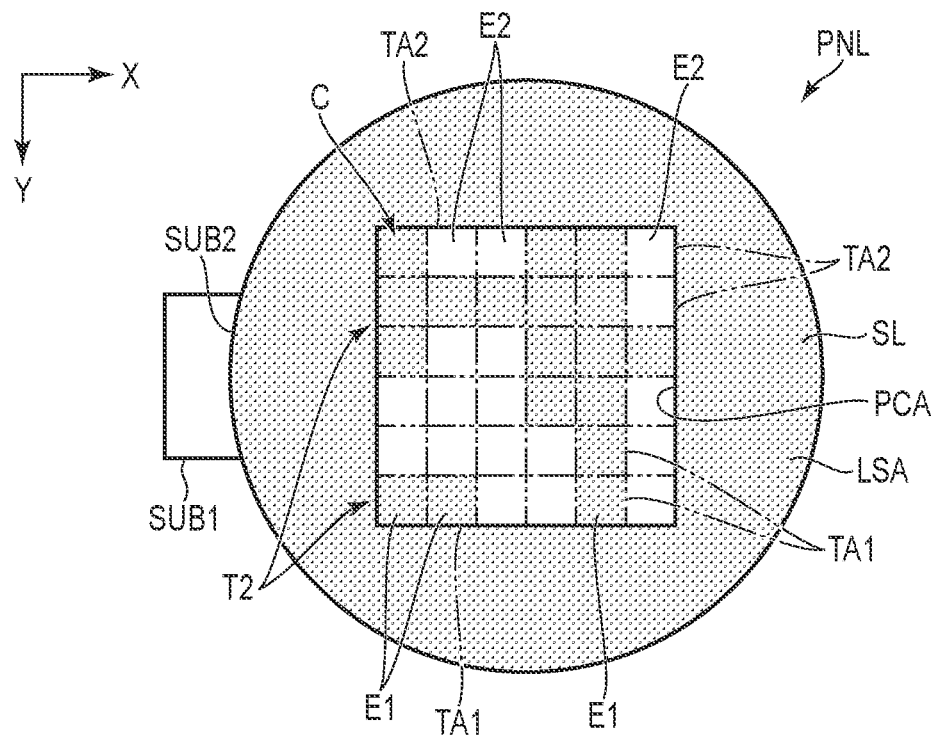
FIG. 22 is a plan view illustrating a liquid crystal panel according to one modified example of the second embodiment.
Figure 23:
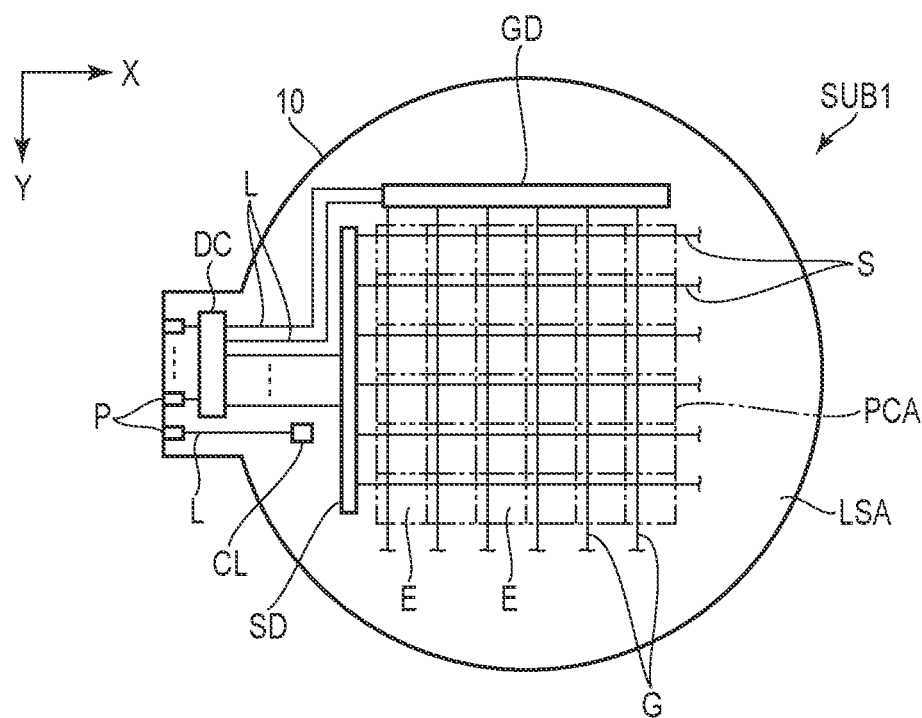
FIG. 23 is a plan view illustrating a first substrate and a driving circuit of the liquid crystal panel according to the modified example.

FIG. 22 is a plan view illustrating a liquid crystal panel PNL according to one modified example of the second embodiment. FIG. 23 is a plan view illustrating a first substrate SUB1 and a driving circuit DC of the liquid crystal panel PNL according to the modified example. In the second embodiment above, the driving circuit DC uses passive driving to drive the plurality of first electrodes E1a and E1b and the plurality of second electrodes E2a, E2b, Etc, and E2d. As per this modified example, the driving circuit DC may use active matrix driving to drive the plurality of electrodes E of the first substrate SUB1 located in the incident light control area PCA.

As illustrated in FIG. 22, the incident light control area PCA of the liquid crystal panel PNL has a plurality of first regions TA1 and a plurality of second regions TA2 arranged in a matrix in the direction X and the direction Y. A plurality of adjacent first regions TA1 constitute the non-transmission region T2, and a plurality of adjacent second regions TA2 constitute the transmission region T1. Further, the first electrode E1 is formed in each of the first regions TA1, and the second electrode E2 is formed in each of the second regions TA2.

The number, size, shape, and the like of the plurality of first regions TA1 and the plurality of second regions TA2 in the incident light control area PCA can be variously modified.

As illustrated in FIG. 23, the liquid crystal panel PNL further includes a plurality of scanning lines G, a plurality of signal lines S, a scanning line driving circuit GD, and a signal line driving circuit SD. The plurality of scanning lines G extend in the direction Y and are arranged side by side at intervals in the direction X. The plurality of signal lines S extend in the direction X and are arranged side by side at intervals in the direction Y. The plurality of signal lines S and the plurality of scanning lines G extend not only in the incident light control area PCA but also in the light shielding area LSA. The plurality of scanning lines G are electrically connected to the scanning line driving circuit GD located in the light shielding area LSA. The plurality of signal lines S are electrically connected to the signal line driving circuit SD located in the light shielding area LSA.

The scanning line driving circuit GD supplies a control signal to a switching element (for example, a thin-film transistor) connected to the electrodes E, via a corresponding one scanning line G among the plurality of scanning lines G. The signal line driving circuit SD supplies a control signal (positive-polarity control signal, negative-polarity control signal, and reference control signal) to the electrodes E via a corresponding one signal line S among the plurality of signal lines S and via the switching element.

The scanning line driving circuit GD and the signal line driving circuit SD are driving circuits for driving the plurality of electrodes E of the incident light control area PCA. The scanning line driving circuit GD and the signal line driving circuit SD are electrically connected to the driving circuit DC via the wiring lines L. The driving of the scanning line driving circuit GD and the signal line driving circuit SD, respectively, is controlled by the driving circuit DC.

The present modified example is also capable of obtaining the same advantageous effects as those of the second embodiment described above.

While certain embodiments have been described, these embodiments have been presented by way of example only, and are not intended to limit the scope of the inventions.

Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

For example, when the imaging device 100 is viewed from a direction perpendicular to the one end surface S1, the liquid crystal panel PNL may cover a part of the illumination device EM or may cover the entire illumination device EM. The imaging device 100 may include a plurality of illumination devices EM. In that case, the plurality of emission ports Oo may be opened in the one end surface S1.

The foregoing embodiments are not limited to or by the foregoing imaging device 100, and can be applied to various imaging devices.

What is claimed is:

1. An imaging device, comprising:
    a housing having a cylindrical shape that includes a central axis, and an emission port and an incident port that are opened in one end surface in a direction along the central axis;
    an illumination device that is accommodated in the housing, and that faces the emission port and illuminates a front side of the one end surface through the emission port;
    an optical system that is accommodated in the housing, and that faces the incident port and has at least one lens;
    a liquid crystal panel that is located closer to the outside of the housing than the optical system, and that has an incident light control area and covers each of the entire incident port and the entire optical system when viewed from a direction perpendicular to the one end surface; and
    an imaging element that is accommodated in the housing, that constitutes a camera together with the optical system, and that acquires information about light falling incident from outside the housing through the incident port, the incident light control area of the liquid crystal panel, and the optical system,
    wherein
    the incident light control area has a first region, a second region located so as to be shifted from the first region, and a third region other than the first region and the second region,
    the liquid crystal panel alternately switches the incident light control area between a first light control pattern and a second light control pattern,
    when switching to the first light control pattern, the liquid crystal panel sets the first region to a non-transmissive state, and sets each of the second region and the third region to a transmissive state, and
    when switching to the second light control pattern, the liquid crystal panel sets the second region to a non-transmissive state, and sets each of the first region and the third region to a transmissive state.

2. The imaging device according to claim 1, further comprising:
    a controlling circuit that controls driving of the illumination device, the liquid crystal panel, and the imaging element,
    wherein
    the controlling circuit acquires first image information acquired by performing first imaging of a subject by using the liquid crystal panel with the first light control pattern, and using the optical system, and the imaging element,
    the controlling circuit acquires second image information acquired by performing second imaging of the subject by using the liquid crystal panel with the second light control pattern, and using the optical system, and the imaging element, and
    the controlling circuit derives an image of the subject and a distance from the imaging element to the subject based on the first image information and the second image information.

3. The imaging device according to claim 1, wherein the liquid crystal panel further switches the incident light control area to a light transmission pattern, and
    when switching to the light transmission pattern, the liquid crystal panel sets all of the first region, the second region, and the third region to a transmissive state.

4. The imaging device according to claim 1, further comprising:
    a driving circuit,
    wherein
    the liquid crystal panel further includes:
        a first substrate having a first electrode located in the first region, a second electrode located in the second region, and a third electrode located in the third region;
        a second substrate disposed so as to face the first substrate with a gap therebetween; and
        a liquid crystal layer located in the incident light control area and held between the first substrate and the second substrate,
    the driving circuit drives the first electrode, the second electrode, and the third electrode, and
    the driving circuit performs polarity inversion driving by taking, as targets, at least the first electrode and the second electrode.

5. The imaging device according to claim 4, further comprising:
    a controlling circuit that controls driving of the illumination device, the liquid crystal panel, and the imaging element,
    wherein
    the second substrate has a counter-electrode located in the incident light control area, and
    the controlling circuit applies a common voltage to the counter-electrode.

6. The imaging device according to claim 1, wherein the emission port and the incident port each have a circular shape.

7. The imaging device according to claim 6, wherein when the emission port and the incident port are viewed from a direction parallel to the central axis, the size of the incident port is larger than the size of the emission port.

8. The imaging device according to claim 6, wherein the emission port and the incident port are arranged side by side in a diametrical direction of the one end surface.

9. The imaging device according to claim 8, further comprising:
    a wiring substrate accommodated in the housing,
    wherein
    the liquid crystal panel is accommodated in the housing, and the wiring substrate is coupled to the liquid crystal panel in an area spaced apart from the optical system in a cross direction intersecting the diametrical direction.

* * * * *